US00PP34424P2

(12) United States Plant Patent
Hartman

(10) Patent No.: US PP34,424 P2
(45) Date of Patent: Jul. 12, 2022

(54) ***CALADIUM* PLANT NAMED 'RIB OF15-809 RD'**

(50) Latin Name: ***Caladium* X *hortulanum***
Varietal Denomination: 'RIB OF15-809 RD'

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/571,467

(22) Filed: Jan. 8, 2022

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/02; A01H 5/12
See application file for complete search history.

*Primary Examiner* — Kent L Bell
(74) *Attorney, Agent, or Firm* — C. Anne Whealy

(57) ABSTRACT

A new and distinct cultivar of *Caladium* plant named 'RIB OF15-809 RD', characterized by its compact and upright to outwardly arching plant habit; dense and bushy appearance; vigorous growth habit and rapid growth rate; upright, narrow and undulate lance-type leaves that are dark red in color with dark green-colored margins; petioles that are tannish pink in color with brown-colored stippling, streaks and tessellations; and good garden performance and tolerance to high light conditions.

3 Drawing Sheets

Figure 1:
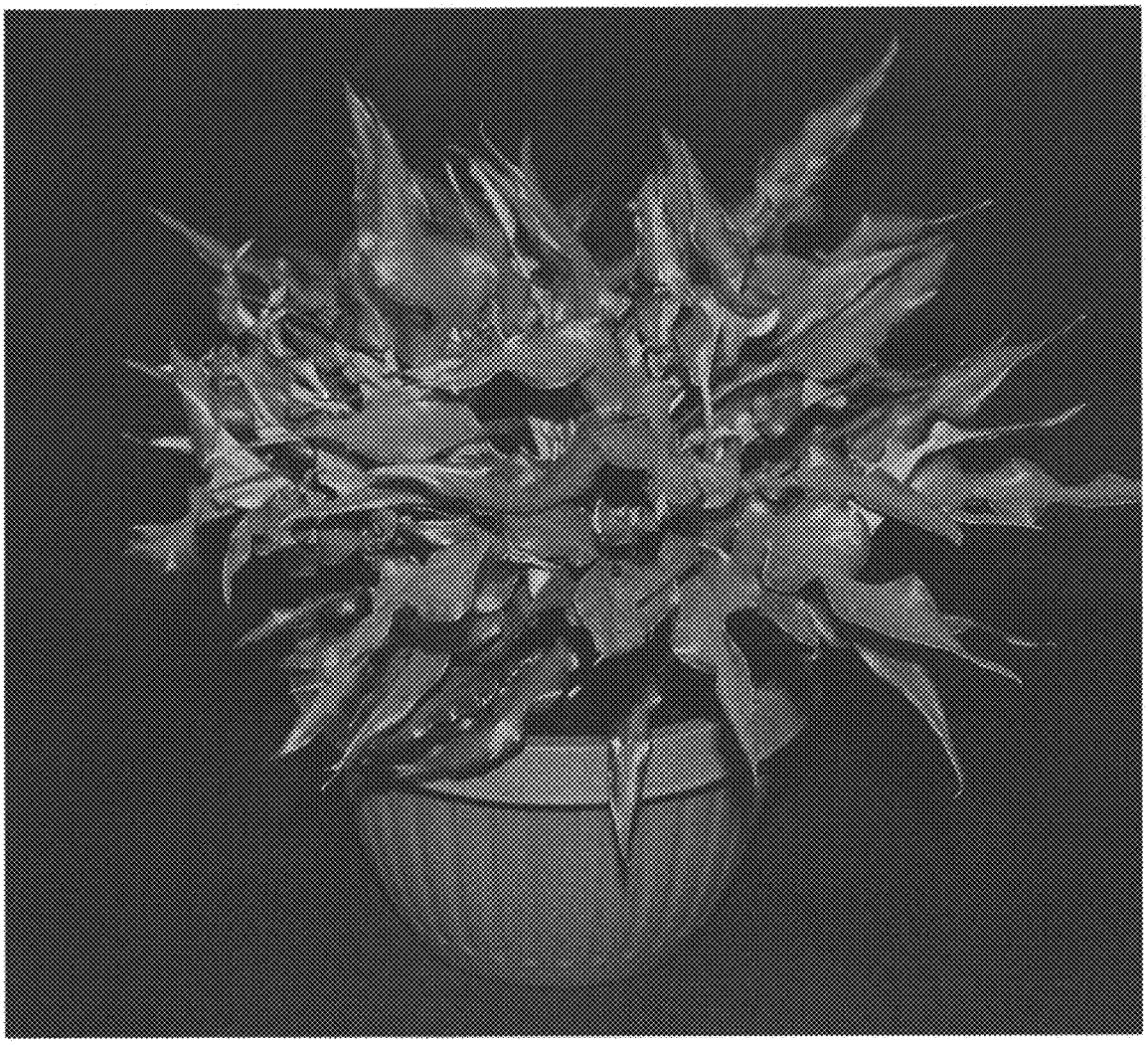

Botanical designation: *Caladium* X *hortulanum.*
Cultivar denomination: 'RIB OF15-809 RD'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'RIB OF15-809 RD'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2014 in Avon Park, Fla. of *Caladium* X *hortulanum* 'Florida Red Ruffles', disclosed in U.S. Plant Pat. No. 13,136, as the female, or seed, parent with *Caladium* X *hortulanum* 'Red Frill', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2015.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2016 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RIB OF15-809 RD'. These characteristics in combination distinguish 'RIB OF15-809 RD' as a new and distinct *Caladium* plant:

1. Compact and upright to outwardly arching plant habit; dense and bushy appearance.
2. Vigorous growth habit and rapid growth rate.
3. Upright, narrow and undulate lance-type leaves that are dark red in color with dark green-colored margins.
4. Petioles that are tannish pink in color with brown-colored stippling, streaks and tessellations.
5. Good garden performance and tolerance to high light conditions.

Plants of the new *Caladium* differ primarily from plants of the female parent, 'Florida Red Ruffles', in the following characteristics:

1. Plants of the new *Caladium* are more upright than and not as mounding as plants of 'Florida Red Ruffles'.
2. Leaves of plants of the new *Caladium* are more narrow and more undulate than leaves of plants of 'Florida Red Ruffles'.
3. Leaves of plants of the new *Caladium* are more upright than leaves of plants of 'Florida Red Ruffles'.
4. Leaf petioles of plants of the new *Caladium* are tannish pink in color with brown-colored stippling, streaks and tessellations whereas leaf petioles of plants of 'Florida Red Ruffles' are almost black in color with tannish pink-colored stripes.

Plants of the new *Caladium* differ primarily from plants of the male parent, 'Red Frill', in the following characteristics:

1. Plants of the new *Caladium* are more upright than and not as mounding as plants of 'Red Frill'.
2. Leaves of plants of the new *Caladium* are more narrow and more undulate than leaves of plants of 'Red Frill'.
3. Leaves of plants of the new *Caladium* are more upright than leaves of plants of 'Red Frill'.

Plants of the new *Caladium* can be compared to plants of *Caladium* X *hortulanum* 'Heart's Delight', disclosed in U.S. Plant Pat. No. 23,992. In side-by-side comparisons, plants of the new *Caladium* differ primarily from plants of 'Heart's Delight' in the following characteristics:

1. Plants of the new *Caladium* are more compact and upright than and not as mounding as plants of 'Heart's Delight'.
2. Leaves of plants of the new *Caladium* are more narrow and more undulate than leaves of plants of 'Heart's Delight'.
3. Leaves of plants of the new *Caladium* are more upright than leaves of plants of 'Heart's Delight'.
4. Leaves of plants of the new *Caladium* are dark red in color with dark green-colored margins whereas leaves of plants of 'Heart's Delight' have red-colored venation, greyed purple-colored interveinal areas and mottled light and dark green-colored borders.
5. Leaf petioles of plants of the new *Caladium* are tannish pink in color with brown-colored stippling, streaks and tessellations whereas leaf petioles of plants of 'Heart's Delight' are green in color tinged with pink and varying brown-colored streaks and stripes.

Plants of the new *Caladium* can also be compared to plants of *Caladium* X *hortulanum* 'UF 4424', disclosed in U.S. Plant Pat. No. 25,598. In side-by-side comparisons, plants of the new *Caladium* differ primarily from plants of 'UF 4424' in the following characteristics:

1. Plants of the new *Caladium* are more upright than and not as mounding as plants of 'UF 4424'.
2. Leaves of plants of the new *Caladium* are more narrow and more undulate than leaves of plants of 'UF 4424'.
3. Leaves of plants of the new *Caladium* are more upright than leaves of plants of 'UF 4424'.
4. Leaf petioles of plants of the new *Caladium* are tannish pink in color with brown-colored stippling, streaks and tessellations whereas leaf petioles of plants of 'UF 4424' are greyed red in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'RIB OF15-809 RD' grown in a container that has not had its tuber de-eyed.

Figure 2:
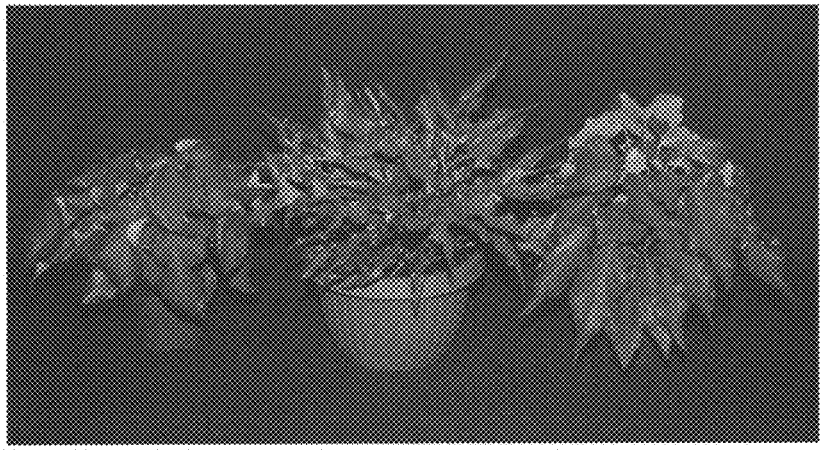

The photograph at the top of the second sheet (FIG. 2) is side perspective view of typical plants of the female parent, 'Florida Red Ruffles' (left), 'RIB OF15-809 RD' (center) and the male parent, 'Red Frill' (right).

Figure 3:
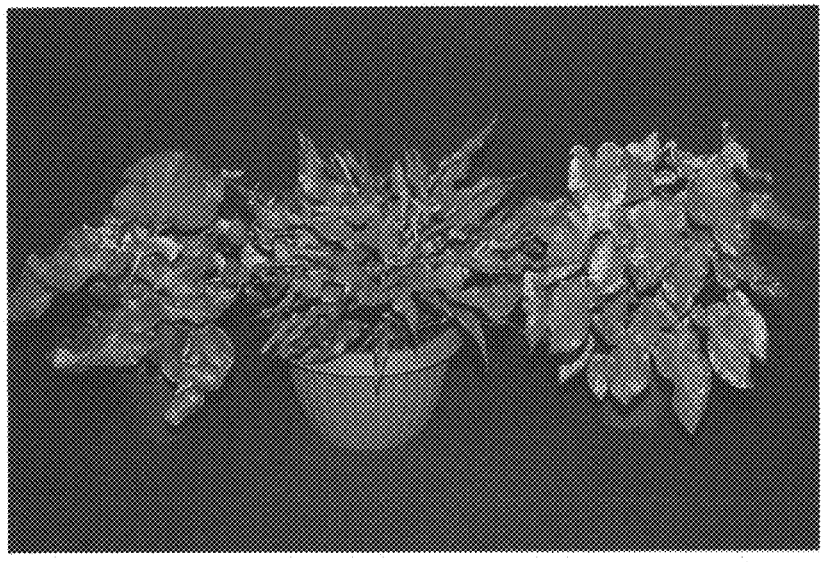

The photograph at the bottom of the second sheet (FIG. 3) is side perspective view of typical plants of 'UF 4424' (left), 'RIB OF15-809 RD' (center) and 'Heart's Delight' (right).

Figure 4:
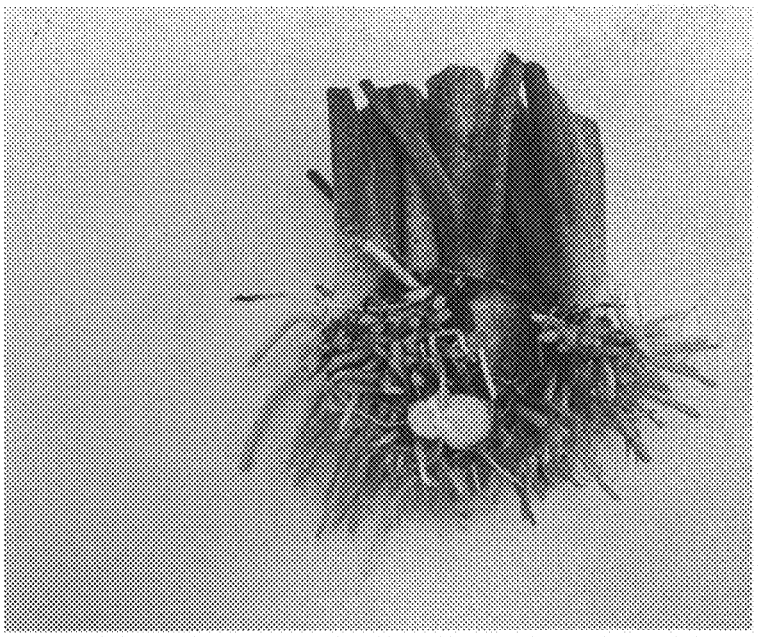

The photograph at the top of the third sheet (FIG. 4) is a close-up view of typical freshly-harvested tubers with roots and leaf petioles of 'RIB OF15-809 RD'.

Figure 5:
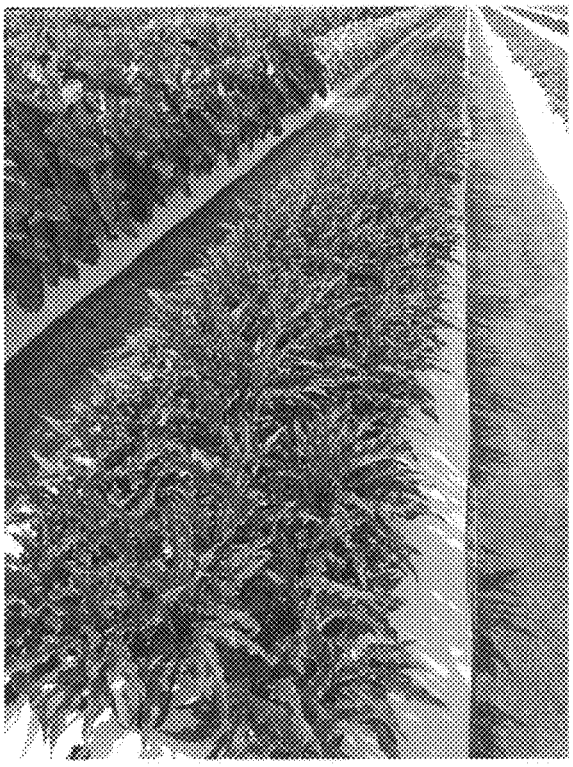

The photograph at the bottom of the third sheet (FIG. 5) is a side perspective view of typical plants of 'RIB OF15-809 RD' grown in an open production field.

DETAILED BOTANICAL DESCRIPTION

The aforementioned photographs and following observations and measurements describe plants grown in 25-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 23° C. to 26° C., night temperatures ranged from about 22° C. to 25° C. and light levels were about 1,300 μmol. During the production of the outdoor nursery-grown plants, day temperatures ranged from about 29° C. to 35° C., night temperatures ranged from about 28° C. to 33° C. and under full sunlight conditions. Plants grown in the shade house were nine weeks old and plants grown in the outdoor nursery were six months old when the photographs and the detailed description were taken. Plants used in the photographs and detailed description did not have their tubers de-eyed. In the following description, color references are made to The Royal Horticultural Society Colour Chart, 2015 Edition, except where general terms of ordinary dictionary significance are used.

Botanical classification: *Caladium* X *hortulanum* 'RIB OF15-809 RD'.

Parentage:

*Female, or seed, parent.*—*Caladium* X *hortulanum* 'Florida Red Ruffles' disclosed in U.S. Plant Pat. No. 13,136.

*Male, or pollen, parent.*—*Caladium* X *hortulanum* 'Red Frill', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments are elliptic in shape. Height: About 4.1 cm. Diameter: About 5.2 cm to 7 cm. Segment height: About 1.9 cm to 2.1 cm. Segment diameter: About 1.9 cm to 2.4 cm. Axillary bud shape: Roughly triangular. Axillary bud size: About 4 mm by 5 mm. Tuber texture: Thick, starchy; somewhat brittle. Color: Periderm, freshly-harvested: Close to 199A. Periderm, dried: Close to 200A. Epidermis: Close to 158D. Cortical tissue: Close to 4D. Axillary buds: Close to 36C and 36D. Root description: Thick, fleshy contractile roots with few lateral branches; color, close to 155C. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Compact and upright to outwardly arching plant habit; dense and bushy appearance; vigorous growth habit and rapid growth rate; potted plants finish in saleable form in about nine weeks after planting tubers; leaf petioles and leaves arise from one or more growing points on tubers; leaf petioles initially upright and outwardly arching with development; about two to three leaves per primary shoot.

*Plant height, from soil level to top of foliar plane, shade house-grown potted plants*.—About 25 cm to 32 cm.

*Plant diameter or spread, shade house-grown potted plants*.—About 40 cm to 49 cm.

*Cataphylls, shade house-grown potted plants*.—Length: About 3 cm to 4.5 cm. Width: About 1.2 cm to 1.8 cm. Shape: Ligulate to somewhat wedge-shaped. Apex: Acuminate to acute. Base: Sheathing the stem. Color, inner surface: Close to N155D; venation tinged with close to N200A. Color, outer surface: Close to 199C tinged with close to 147C and densely streaked and stippled with close to 200A tinged with close to 147A; color becoming closer to 200B to 200C with subsequent development.

Leaf description:

*Arrangement and type*.—Alternate; simple; narrow lance-type.

*Length, shade house-grown potted plants, flattened*.—About 12 cm to 17 cm.

*Width, shade house-grown potted plants, flattened*.—About 4.5 cm to 6.7 cm.

*Shape*.—Lanceolate.

*Apex*.—Acuminate to acute, long-tapered and apiculate.

*Base*.—Sagittate; involute.

*Margin*.—Entire; very wavy with broad undulations.

*Texture and luster, upper surface*.—Smooth, glabrous; slightly glossy; relatively thick, coriaceous and rigid.

*Texture and luster, lower surface*.—Smooth, glabrous; glaucous; dull sheen.

*Venation pattern*.—Pinnate and palmate.

*Color, shade house-grown potted plants*.—When developing and fully expanded leaves, upper surface: Interveinal areas: Close to 46C with occasional and variable spots and streaks, close to N155C. Margins: Close to between 139A and N189A and edges, close to 187A. Basal margin: Close to 53A tinged with close to 187A. Midvein: Close to 53A. Lateral venation: Close to 46A flushed with close to N187A. When developing and fully expanded leaves, lower surface: Interveinal areas: Slightly glaucous; close to 53A tinged with close to 185A; occasional and variable spots and streaks, close to 191A surrounded by close to 160C. Margins: Close to 191A and 189A with edges, close to 187A. Midvein: Slightly glaucous, close to 182B and densely streaked with close to 53A tinged with close to 185A. Primary veins: Slightly glaucous, close to 191A tinged with close to N187A. Secondary veins: Slightly glaucous, close to 189A.

*Petioles*.—Aspect: Initially upright and straight and outwardly arching with development; flexible. Length, shade house-grown potted plants: About 12 cm to 22 cm. Diameter, distally, shade house-grown potted plants: About 3 mm to 3.5 mm. Diameter, proximally, shade house-grown potted plants: About 4 mm to 6 mm. Texture and luster: Smooth, glabrous; glaucous; dull sheen. Color, shade house-grown potted plants: Close to N170D, 199D, 182D and 147C with stippling, streaks and tessellations of close to 147A tinged with close to 200A and N200A; just below leaf junction, may also be flushed with close to 182B to 182C. Wing length, shade house-grown potted plants: About 3 cm to 4.5 cm. Wing diameter, shade house-grown potted plants: About 8 mm. Texture and luster, inner and outer surfaces: Smooth, glabrous; slightly glossy. Wing color, shade house-grown potted plants: Inner surface: Close to N155D; colors and patterns on the outer surface are visible on the inner surface. Outer surface: Close to 199C tinged with close to 147C with stippling and streaks, close to 200A tinged with close to 147A.

Inflorescence description: To date, inflorescence development has not been observed on plants of the new *Caladium*.

Pathogen tolerance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'RIB OF15-809 RD' as illustrated and described.

* * * * *